US008401260B2

(12) United States Patent
Nirmal et al.

(10) Patent No.: US 8,401,260 B2
(45) Date of Patent: Mar. 19, 2013

(54) SYSTEMS AND METHODS FOR ANALYZING GROWTH OF COMPUTER DETECTED PATTERNS ON DIGITAL MEDICAL IMAGES

(75) Inventors: Davis V. Nirmal, Bangalore (IN); George Joji, Bangalore (IN)

(73) Assignee: General Electric Company, Schenectady, NY (US)

(*) Notice: Subject to any disclaimer, the term of this patent is extended or adjusted under 35 U.S.C. 154(b) by 948 days.

(21) Appl. No.: 12/235,236

(22) Filed: Sep. 22, 2008

(65) Prior Publication Data
US 2010/0074481 A1 Mar. 25, 2010

(51) Int. Cl.
*G06K 9/00* (2006.01)
(52) U.S. Cl. .................................................. 382/128
(58) Field of Classification Search .................. None
See application file for complete search history.

(56) References Cited

U.S. PATENT DOCUMENTS

| | | | |
|---|---|---|---|
| 6,484,047 B1 | 11/2002 | Vilsmeier | |
| 6,909,792 B1 | 6/2005 | Carrott et al. | |
| 6,970,587 B1* | 11/2005 | Rogers | 382/132 |
| 7,043,068 B2 | 5/2006 | Labudde | |
| 7,308,126 B2* | 12/2007 | Rogers et al. | 382/132 |
| 7,639,890 B2* | 12/2009 | Kuriathungal et al. | 382/260 |
| 7,783,094 B2* | 8/2010 | Collins et al. | 382/128 |
| 2004/0184646 A1* | 9/2004 | Oosawa | 382/128 |
| 2005/0251013 A1* | 11/2005 | Krishnan et al. | 600/407 |
| 2006/0274928 A1* | 12/2006 | Collins et al. | 382/132 |
| 2007/0092142 A1* | 4/2007 | Kuriathungal et al. | 382/209 |
| 2007/0100226 A1 | 5/2007 | Yankelevitz et al. | |

* cited by examiner

*Primary Examiner* — Jermele M Hollington

(57) ABSTRACT

Methods and systems are provided for displaying the change in size of a CAD identified pattern over time. Patterns on medical images stored in a medical imaging database are identified and measured using a CAD system. A user interface provides users with access to the medical images stored in imaging database via a network. A medical image belonging to a patient historical exam category and having at least one CAD identified pattern is displayed to a user via the user interface. The size of the CAD identified image pattern and the medical exam date associated with the medical image is compiled for each of the medical images belonging to the patient historical exam category. A graphic is then generated showing the sizes of the CAD identified image pattern and the medical exam dates associated with the medical image.

20 Claims, 4 Drawing Sheets

SYSTEMS AND METHODS FOR ANALYZING GROWTH OF COMPUTER DETECTED PATTERNS ON DIGITAL MEDICAL IMAGES

RELATED APPLICATIONS

[Not Applicable]

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

The presently described technology generally relates to a system and method for improved medical imaging. Particularly, the presently described technology relates to a more efficient system and method for interpreting medical images.

Medical diagnostic imaging systems encompass a variety of imaging modalities, such as x-ray systems, computerized tomography (CT) systems, ultrasound systems, electron beam tomography (EBT) systems, magnetic resonance (MR) systems, and the like. Medical diagnostic imaging systems generate images of an object, such as a patient, for example, through exposure to an energy source, such as x-rays passing through a patient. The generated images may be used for many purposes such as detecting internal defects in an object, for example. Additionally, changes in internal structure or alignment may be determined. Fluid flow within an object may also be represented. Furthermore, the image may show the presence or absence of objects in an object. The information gained from medical diagnostic imaging has applications in many fields, including medicine and manufacturing.

An example of a medical diagnostic imaging system is Picture Archival Communication Systems (PACS). PACS is a term for equipment and software that permits images and information, such as x-rays, ultrasound, computerized tomography (CT), electron beam tomography (EBT), magnetic resonance (MR), or nuclear medicine for example, to be electronically stored, communicated and displayed for viewing. Images from an exam may be viewed immediately, stored, or transmitted. The images may be viewed on diagnostic workstations by users, for example, radiologists.

Computer aided detection, (also referred to as computer assisted detection, or "CAD") is a software tool used in medical science that supports medical practitioners such as radiologists in making interpretations and findings from medical images. Imaging techniques medical imaging systems yield a great deal of information, and a radiologist has to analyze and evaluate a great deal of images comprehensively in a short amount of time. CAD systems can scan a series of medical images for typical appearances. By scanning a series of images from a medical imaging system such as PACS, CAD can recognize patterns in the images. For example, CAD may recognize a healthy tissue pattern by scanning multiple images in a medical imaging system. Based upon the patterns, CAD can identify conspicuous sections in a particular image, for example, images that differ from the healthy tissue patterns, thereby identifying possible problem areas such as diseases, lesions, tumors or the like.

Presently, CAD findings are reported in a structured report ("SR") that contains information about the image identifier, type of finding, pattern, size and coordinates. For example, a SR may indicate that a mammography study was performed, and that an irregularity was located at a particular coordinate address which is possibly a mass lesion. Display applications in the CAD system apply the SR on the images at the time of reading, so that the user can see the CAD findings with a simple click of a mouse button. For example, when viewing an image, a user may click a mouse button on the user interface that causes the identified problem areas to become highlighted.

During review of a CAD report, however, a radiologist cannot see how a problem area has changed over time. For example, CAD may identify a calcification mass from a mammogram study, but it does not have the ability to not how that mass has grown, shrunk or otherwise changed over time. Presently, the only way to make such an analysis is to manually look at each CAD finding in a historical study for a patient and compare them. This can be a time consuming process for a radiologist, and it gives rise to human error, for example, the radiologist may fail to identify the problem area in previously scanned images. Furthermore, ignoring a pattern growth rate for certain afflictions may cause a practitioner to misdiagnose, or fail to recognize the urgency of a particular disease.

Therefore, a need exists for a system and method that allows a user to easily review the change of a problem area in a patient over time. Such a system and method may provide charts, diagrams and other data for practitioner reference. Such a system and method may assist a practitioner in providing proper diagnoses and treatments, while reducing the time necessary to review multiple medical images.

BRIEF SUMMARY OF THE INVENTION

Certain embodiments present a method for displaying the change in size of a CAD identified pattern over time. The steps of the method comprise identifying patterns on medical images stored in a medical imaging database and determining the size of said patterns using a CAD system. In certain embodiments, each of said medical images have a medical exam date associated with the image. Next, a user interface is provided on a computer workstation, the interface having access to the medical images stored in the medical imaging database via a network. Next, at least one medical image is displayed to a user via the user interface, the displayed medical image belonging to a patient historical exam category and having at least one CAD identified pattern. Next, the size of the CAD identified image pattern and the medical exam date associated with the medical image is compiled for each of the medical images stored in the medical imaging database belonging to the patient historical exam category. A graphic is then generated showing the sizes of the CAD identified image pattern and the medical exam dates associated with the medical image for all of the medical images belonging to the patient historical exam category. In certain embodiments, the graphic is displayed on the user interface upon user instruction. For example, the user may display the graphic by moving or hovering a mouse cursor over the displayed CAD identified image pattern.

The present technology also presents a system for visually presenting the size of a CAD identified image pattern over time to a user via a user interface. In certain embodiments, the system comprises a medical imaging database storing a plurality of digital medical images, where each of the digital medical images belongs to a patient historical exam category and has a medical exam date associated with the image. The system also comprises a CAD system identifying patterns on the digital medical images and determining the size of the patterns. In certain embodiments, the system comprises a user interface for presenting at least one digital medical image to a user via a workstation, and a tracking application for compiling information pertaining to the size of a CAD identified image pattern and the medical exam date for all images belonging to the historical exam category of the at least one digital medical image presented by the user interface. The tracking application generates a graphic depicting a comparison of the size of the CAD identified image with respect to the medical exam date for all digital images belonging to the historical exam category of the digital medical image presented by the user interface.

Figure 1:
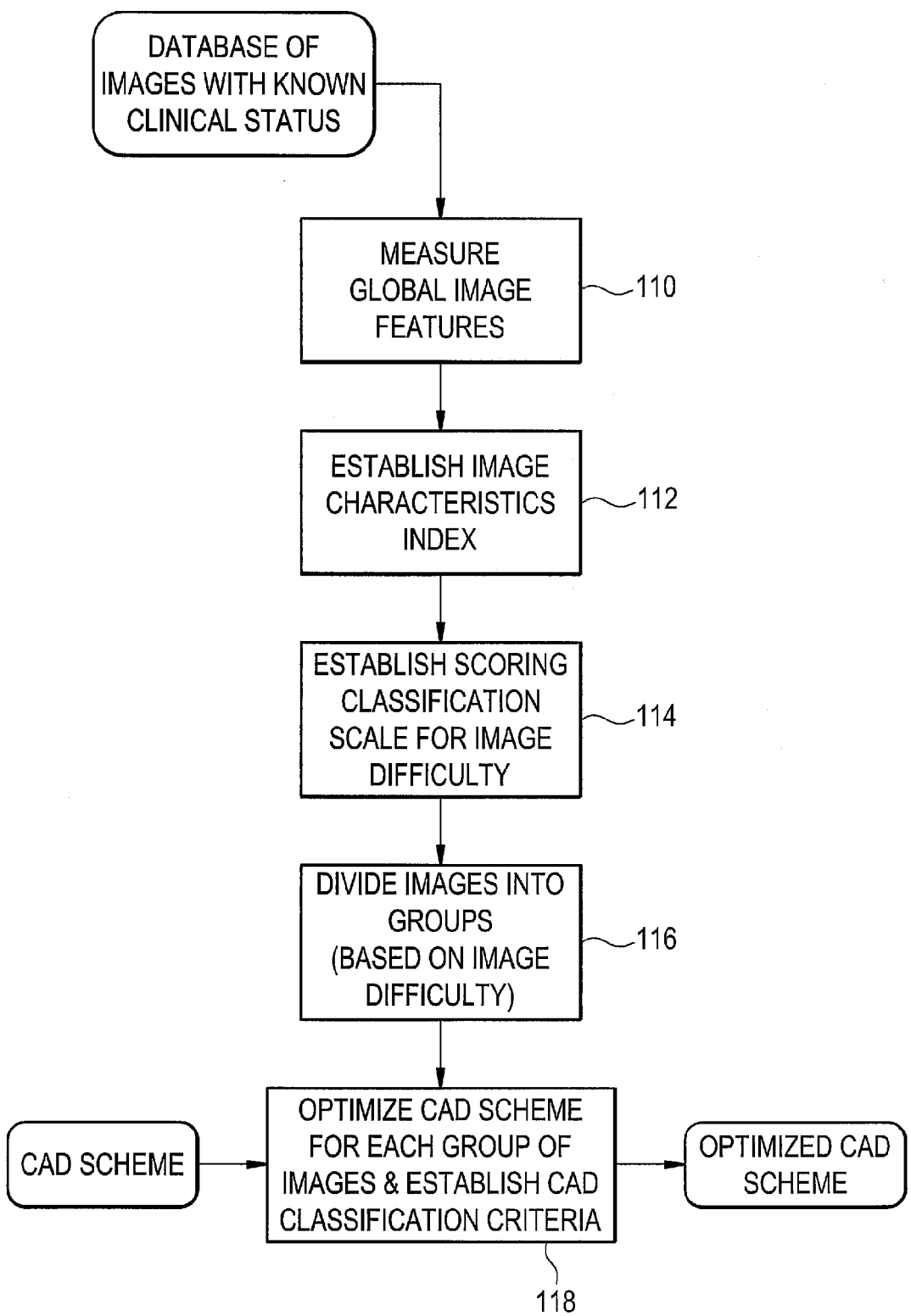
FIG. 1 illustrates a flow diagram of the operation of a CAD system in accordance with the present technology.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

Preliminarily, it should be noted that, while a particular system and method is described in detail herein for analyzing medical imaging data, such as radiology data, this is not by way of limitation, but solely for the purposes of illustration, and the invention may also be employed for analyzing data of other types.

The present technology builds on advances in imaging technology that have now made it possible to scan problem areas such that the entire problem area is imaged. There have been significant improvements in the methods for the measurement of size of problem areas from CT images by using 3D volumetric computer algorithms. In addition, images are not obtained isotropically, meaning that the resolution is nearly the same in the x, y, and z dimensions. Advanced image processing allows for improved segmentation of the problem areas from surrounding structures, with better definition of the problem area boundaries, thus leading to improved measurements. Certain embodiments of the present technology provide systems and methods for monitoring the change in patterns identified on medical images. More specifically, certain embodiments of the presently described technology provide systems and methods for charting the change in size of a medical affliction identified by a CAD system.

CAD is a useful tool that generates reports helping medical practitioners diagnose and treat patients based on reads of medical imaging scans. For example, CAD reports can help radiologists during the diagnostic read of medical images taken during mammography scans, X-ray scans or CT Chest scans. While reading the images, the practitioner can more readily discover patterns in the image that are likely to represent identified problem areas such as diseases or diseased tissue, lesions, tumors, scar tissue or the like. The presently described technology presents systems and methods that provide practitioners with historical data on the change in the identified patterns or problem areas.

The present technology operates in two phases. The first phase consists of adapting and optimizing a CAD scheme based on global features of known images. This may be done in a variety of ways known to those of skill in the art, as is described below. The second phase consists tracking the CAD reports for a particular patient, or a particular medical issue over time. The adaptive phase can be repeated as new images are added to the set of known images, thereby improving the adaption.

An example of an adaptive process of the first phase known by those skilled in the art is described first with reference to FIG. 1. For each image in a database comprising images of patients with known clinical status, that is, in a database of images that have been reviewed and identified with results, global image features and characteristics are computed at step 110. Based on the image feature distributions of all images in the image database, image global characteristics indices are established for each image at step 112. Next a scoring classification scale for global image characteristics is established at step 114, after which the images are divided into a number of groups based on the scores of image characteristics in step 116. Then, for each group of images, the CAD scheme is optimized independently and image based classification criteria for the detection of depictions of abnormal tissue (for example, solid masses or clusters of microcalcifications) for each group are established at step 118.

Figure 2:
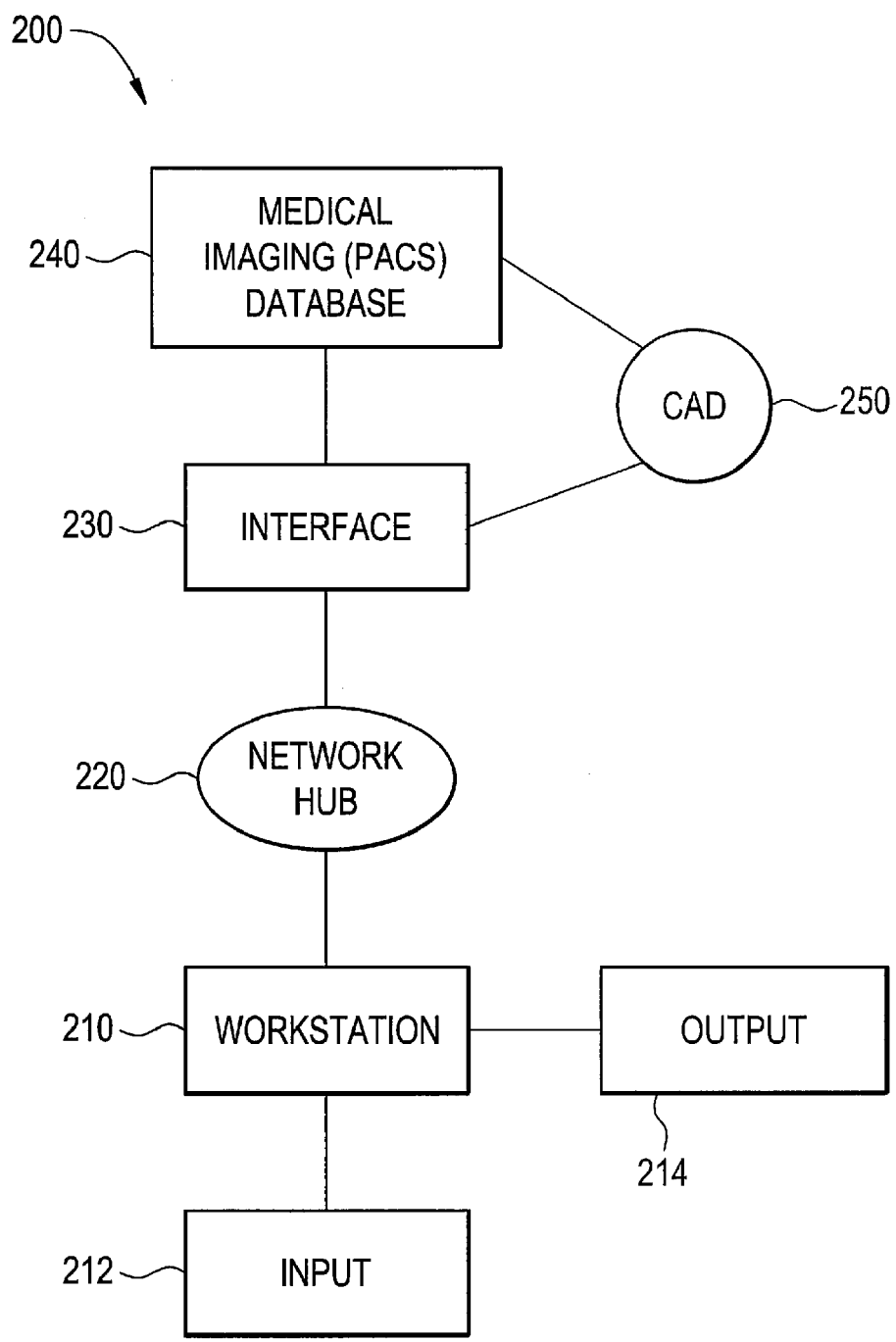
FIG. 2 illustrates a flow diagram of a system presenting images processed by a CAD system to a user.

Thus, using this method, CAD can detect problem areas from identified patterns on digital medical images. FIG. 2 depicts a schematic of the operation of a medical imaging system 200 for reviewing medical images using a CAD program. A workstation 210, such as a computer, comprising an input 212 and an output 214 is connected to the system 200 via a network hub 220. In certain embodiments, the network hub 220 may be the internet, or a means of connecting to the internet or a network, such as an internet router, a network server or a wireless internet connection, for example. A plurality of workstations 200 may be connected to the system 200 via the network hub 220, though there may only be one workstation 210 connected in certain embodiments.

A user interface 230 provides a user of the workstation 210 with interactive access to the system 200. The user may interact with the interface via the input 212, which may be a keyboard, a mouse or any other form of communicating with a workstation, and the output 214 which may be a display such as a monitor, a printer, a telephone line or any other form of delivering communication to a workstation. The interface 230 may offer various applications allowing a user to view, edit, manipulate or otherwise interact with digital images. For example, the interface 230 may offer a medical image viewer allowing a user to view a series of CT scans taken on a patient via a workstation 210. In certain embodiments, the user may be able to manipulate the images via the workstation 210, for example, by zooming and or enlarging the image, cropping or editing the display of the image, rotating the image or inserting comments or notes into the metadata of the image, for example. In certain embodiments, the interface 230 may offer a plurality of applications to the user such that the user has access to medical images taken from a variety of different sources.

The interface interacts with a medical imaging database 240, or a plurality of medical imaging databases. The medical imaging database may be a medical diagnostic imaging system such as PACS, or another database comprising one or more medical images stored digitally. Upon instruction from the interface 230, which may come via a prompting from a user via the workstation 210, an image or series of images can be pooled from the database 240 and presented for user interaction via a workstation 210.

A CAD system 250 interacts with the database 240 and the interface 230 to assist a user in identifying patterns in the medical images. The CAD system 250 can observe all of the images in the database and identify similarities in similar images. For example, the CAD system may identify patterns that occur in all images taken during a mammography study stored in the database 240. The CAD system 250 may operate using the method described above and depicted in FIG. 1, or it may use another process to identify problem areas on medical images.

Images in the database may be marked for identification purposes. For example, images may be labeled according to the modality or type of imaging (X-ray, CT scan, etc.), the procedure through which the image was taken, the body part, the CAD equipment where post-processing occurred, patient information or other information that may be helpful to identify the images. A particular patient may have a plurality of images associated with various studies performed for that patient. These images can be categorized in patient historical exam category for future reference. For example, a patient may have undergone a mammography study every six months for the previous four years. These images may all belong to a single patient historical exam category. The images can be identified with labels identifying the patient, the date of the study, the time of the study, the equipment used for the study and the results or observations from the study (e.g., the location and size of problem areas such as masses, legions or tumors).

Workstations on medical imaging systems may be capable with connecting to enterprise wide medical imaging systems and databases, and thus have access to every study on the enterprise. Using this mechanism, the workstation applications can pull the relevant historical studies of a patient during practitioner review based on the modality, body part, procedure code or another identification means.

Figure 3:
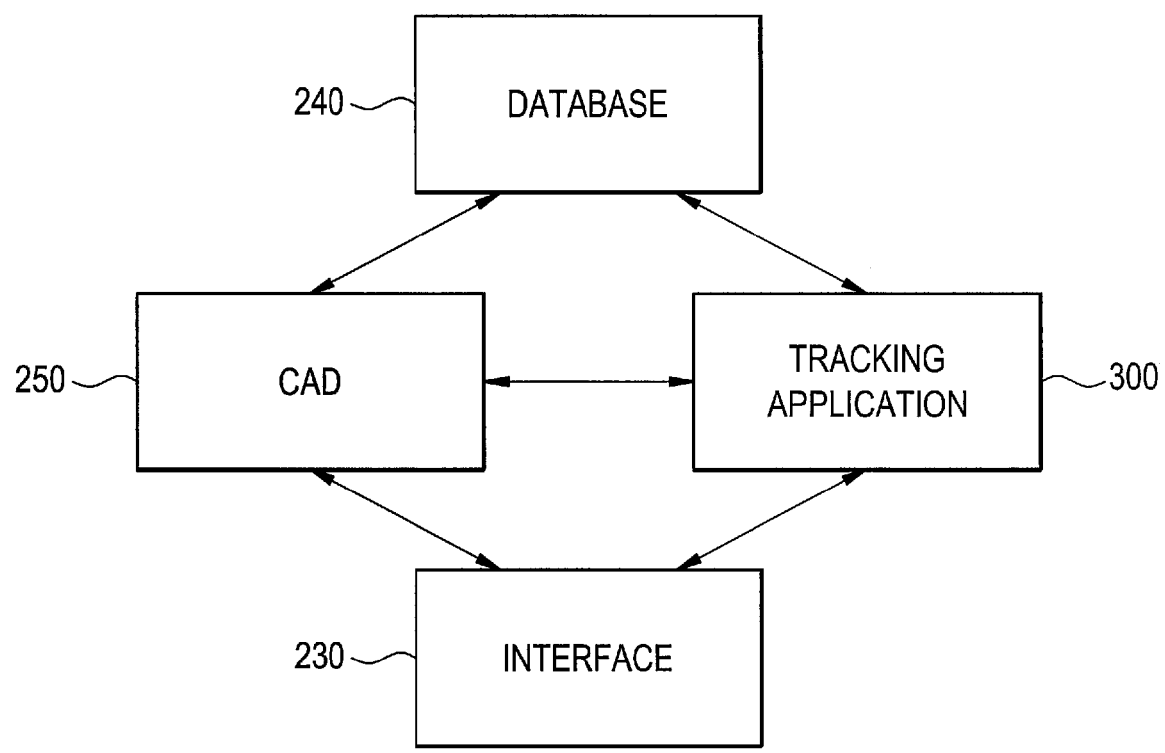
FIG. 3 illustrates a system tracking CAD identified image patterns in accordance with embodiments of the present technology.

In certain embodiments of the present technology, the system 200 comprises a tracking application 300, as shown in FIG. 3. The tracking application 300 is accessible via user interface 230. The tracking application operates with images stored in the image database 240 and compiles information based on CAD reports assigned to the various images from the CAD system 250. In certain embodiments, where a particular patient's historical CAD report data indicates a pattern from a particular type of medical exam (e.g., a mammography exam), the tracking application can generate a graph displaying the size of the problem area as a course of time. For example, the tracking application 300 may compile all information from a patient's historical CAD reports concerning the size of a tumor in mammography studies. The tracking application 300 may generate a table, or a chart that displays a growth line of the pattern. The growth line is a visual indication of the rate at which patterns identified in the image grow or shrink over time. For example, where a pattern is identified to be a mass lesion, the growth line may display the diameter, circumference or radius of the lesion on the Y-axis and the date for which the pattern was imaged on the X-axis.

Figure 4:
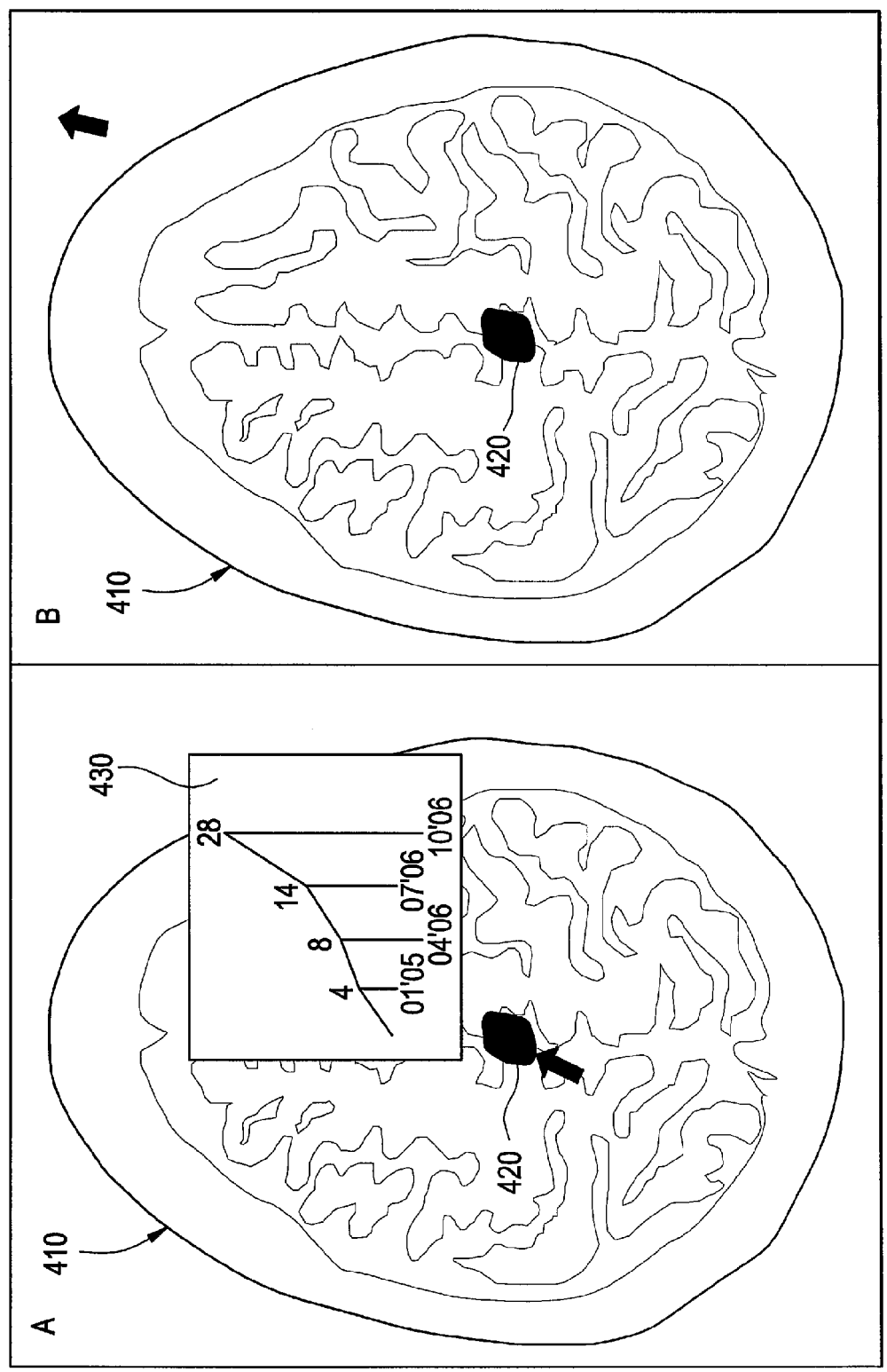
FIG. 4 illustrates a screen shot of a user interface in accordance with one embodiment of the present invention, displaying a graphic based on information compiled about the size and shape of problem areas in CAD reports.

The tracking application compiles information about the size and shape of problem areas identified in CAD reports and generates a graphic to attach to the image based on the previous CAD reports. When the image is viewed by a practitioner or any user at a workstation, the application may display the graphic upon user instruction. FIG. 4 depicts an exemplary screen shot of a user interface operating the tracking application 300. A medical image 410 is displayed via the interface. A pattern 420 or problem area is identified in the center of the image. Upon user instruction, a graphic 430 will appear on the interface. For example, the user may instruct the graphic to appear by clicking on a menu or icon on the interface using an input such as a mouse or a keyboard. Alternatively, the graphic 430 may appear when a user places a mouse cursor over the identified pattern or problem area 420. In certain embodiments, the graphic may appear with or without a click of the mouse. When the mouse cursor is moved away from the pattern 420 or problem area, the graphic disappears, as shown in View B of FIG. 4.

In certain embodiments, the tracking application pulls patient historical data from the medical imaging database to generate the graphic 430 upon user instruction. Alternatively, the tracking application 300 may automatically update each file in the database with the appropriate graphics 430, regardless of whether so instructed by a user. In the alternative embodiment, the tracking application 300 may produce the graphic 430 more quickly, as the graphic would already have been generated.

As stated above, the graphic 430, may be a graph, chart, table, or other visual display showing the size of a pattern in comparison to time. In FIG. 4, the graphic 430 plots the growth of a mass lesion (pattern 420) in millimeters on the Y-axis, and time on the X-axis. The graphic 430 shows that in January of 2006, the pattern had a diameter of 4 mm, and three months later in April of 2006, the pattern had grown to 8 mm. In July of 2006, the pattern had grown to 14 mm, and by October of 2006, 28 mm. Such an example provides important information to a practitioner that the lesion is growing rapidly.

In certain embodiments of the presently disclosed technology, a method is provided for displaying the growth of identified patterns on medical images. First, patterns are identified on medical images stored in a medical imaging database using a CAD system. Patterns may represent medical problem areas, such as diseases or diseased tissue, lesions or mass lesions, tumors, scar tissue or the like. The sizes of the CAD identified patterns are determined using the CAD system and associated with the medical images. The sizes of the CAD identified patterns may be determined based on surface area, volume, diameter, circumference, radius, length, width, mass or any combination thereof. Each medical image also has a medical exam date also associated with the image. The medical exam date represents the date in which the medical image was obtained from the patient. For example, a medical image obtained from a mammography performed on Jun. 21, 2006 will have a medical exam date of Jun. 21, 2006 associated with the image. Accordingly, the size of the CAD identified patterns will have a corresponding date allowing for a comparison of the size of the pattern over time. Furthermore, each image stored in the medical imaging database is assigned to at least one patient exam historical category. For example, an image taken from a mammography of the right breast of Jane Doe will belong to the patient historical category of Jane Doe right breast mammography.

In certain embodiments, the information generated by a CAD system may be stored with the image as a SR report. The SR report may contain information including, but not limited to, patient historical exam category, identified patterns or potential problem areas, the sizes of all identified patterns or problem areas, date of medical exam in which the image was taken, other images belonging to the same patient historical exam category, type of exam, equipment the exam was taken on or the practitioner performing the exam.

Next, a user interface is provided for access by a user on a computer workstation. The user interface has access to the medical images stored in the medical imaging database via a network. For example, a user may select a medical image for viewing from a medical imaging database via the user interface by scrolling through a list of medical images available on the database. For example, a user may open a menu via the interface that displays a list of each image on the medical imaging database and the corresponding patient historical category for the image.

Next, the user interface displays at least one of the medical images to a user via the user interface. In certain embodiments, the image may be displayed using a digital image processor, for example. The displayed medical image may have at least one CAD identified pattern. In certain embodiments the CAD identified image may be highlighted via the interface. For example, a black and white medical image may highlight a CAD identified image in yellow.

In the next step, the size of the CAD identified image patterns and the medical exam dates associated with the images is compiled for each image belonging to the patient historical category of displayed on the user interface. The data may be compiled by gathering the SR reports associated with each image belonging to a patient historical exam category. For example, where the user interface is displaying a medical image belonging to the patient historical category of Jane Doe right breast mammography, the size of each CAD identified image pattern on images belonging to the Jane Doe right breast mammography patient historical category and the corresponding medical exam date for each of the images are compiled. The data may be compiled in the form of a table or a spreadsheet, for example.

Next, the interface generates a graphic that depicts relationship between the size of the CAD identified image pattern and the medical exam dates associated with the medical image for all of the medical images belonging to the patient historical exam category. For example, the interface may generate a line graph where the size of the CAD identified image pattern is charted on the Y-axis vs the medical exam date that the image was taken on the X-axis, as is depicted in FIG. 4. Alternatively, the graphic may be depicted via an alternative graph or chart, such as a bar graph, a point grid, a pie chart, or a data table, for example. In certain embodiments, there may be more than one graphic generated, each graphic associated with a particular CAD identified image pattern. For example, where a medical image has more than one CAD identified image pattern, each CAD identified image pattern may be associated with a unique graphic that represents the growth of the pattern over time.

Next, the user interface displays the graphic upon user instruction. For example, the interface may hide the graphic when the mouse cursor operated by a user is not on or around the CAD identified pattern. Alternatively, the user may click an icon on the interface that instructs the interface to show all graphics. When the user clicks on the icon again, all the displayed graphics may be hidden, for example. In certain embodiments, the user interface may display all graphics at all times.

Thus the disclosed systems and methods provide a user, such as a medical practitioner with a procedure for viewing the growth of CAD identified patterns over time. The disclosed technology provides medical practitioners with a complete view of a pattern's presence on a medical image. The technology depicts the size of the pattern among all the historical patient data with a simple movement of a mouse cursor. The technology provides significant improvement in a practitioner's workflow by providing a complete view on how the problem area represented by the pattern has been growing on a patient. Such improvements help avoid the possibility of medical errors due to practitioner negligence, low visibility of patterns on images, or a lack of knowledge about the history of the pattern.

Those skilled in the art will appreciate that the embodiments disclosed herein may be applied to the formation of any clinical system. Certain features of the embodiments of the claimed subject matter have been illustrated as described herein; however, many modifications, substitutions, changes and equivalents will now occur to those skilled in the art. Additionally, while several functional blocks and relations between them have been described in detail, it is contemplated by those of skill in the art that several of the operations may be performed without the use of the others, or additional functions or relationships between functions may be established and still be in accordance with the claimed subject matter. It is, therefore, to be understood that the appended claims are intended to cover all such modifications and changes as fall within the true spirit of the embodiments of the claimed subject matter.

The invention claimed is:

1. A method for determining a change in size of an identified pattern over time comprising the steps of:
   identifying a pattern on one or more medical images,
   determining a pattern size of said identified pattern using a computer aided detection system;
   associating each of said medical images with a medical exam date;
   placing each of said medical images in a patient category in a medical imaging database;
   displaying a medical image to a user via a user interface, said displayed image having a displayed pattern and said displayed image further belonging to a displayed image patient category; and
   compiling a pattern growth rate for said displayed pattern over time, wherein said pattern grown rate is based on the identified pattern size of the displayed pattern and the medical exam date for each medical image belonging to said displayed image patient category.

2. The method of claim 1, further comprising the step of:
   generating a graphic showing said pattern growth rate and displaying the graphic upon user instruction via the user interface.

3. The method of claim 2, wherein the user instructs the interface to display the graphic by moving a mouse cursor over the identified image pattern.

4. The method of claim 3, wherein the graphic disappears from display when the user moves the mouse cursor away from the identified image pattern.

5. The method of claim 2, wherein the graphic is a two-dimensional line graph charting the size of the identified pattern size on the Y-axis, and the medical exam date associated with the medical image having the corresponding identified pattern size on the X-axis.

6. The method of claim 2, wherein the identified image pattern represents a medical problem area.

7. The method of claim 6, wherein the identified image pattern represents a disease or diseased tissue.

8. The method of claim 6, wherein the identified image pattern represents a mass lesion or a tumor.

9. The method of claim 1, wherein the displayed medical image comprises two or more displayed patterns, and wherein said compiling step compiles a pattern growth rate for each of said displayed patterns.

10. The method of claim 1, wherein the pattern size of the identified image pattern is the circumference of the identified image pattern.

11. The method of claim 1, wherein the pattern size of the identified image pattern is the diameter, radius or width of the identified image pattern.

12. The method of claim 1, wherein the size of the identified image pattern is the 3-dimensional volume of the identified image pattern.

13. A system for visually presenting a change in size of an identified image pattern over time on a digital medical image comprising:
 a medical imaging database storing a plurality of digital medical images, each of the digital medical images belonging to a patient category and having a medical exam date associated with the image;
 a computer aided detection system adapted to identify patterns on the digital medical images and determining the size of the patterns;
 a tracking application adapted to compile a pattern growth rate of an identified pattern over time based on the size of an identified image pattern and the medical exam date associated with one or more images belonging to a patient category; and
 a user interface adapted to display at least one of digital medical image, said displayed digital medical image having a displayed image identified pattern;
  wherein said user interface is adapted to display a graphic depicting the pattern growth rate of said displayed image identified pattern.

14. The system of claim 13, wherein the user interface displays said graphic upon user instruction.

15. The system of claim 14, wherein said user interface is further adapted to allow a user to instruct the user interface to display said graphic by moving a mouse cursor over an identified image pattern.

16. The system of claim 14, wherein said user interface is further adapted to allow a user to instruct the user interface to display said graphic by clicking on an icon provided by the user interface.

17. The system of claim 13, wherein said graphic is a graph that plots the identified pattern size on the Y-axis and the medical exam date in which the identified pattern size was observed on the X-axis.

18. The system of claim 17, wherein the image pattern size is at least one of the radius, the diameter, the circumference, the width or the height of the identified image pattern.

19. The system of claim 13, wherein the identified image pattern represents a mass lesion identified from a mammography exam.

20. The system of claim 13, wherein the medical image database is a picture archival communication system.

* * * * *